United States Patent
Nanba et al.

[11] Patent Number: 5,096,629
[45] Date of Patent: Mar. 17, 1992

[54] METHOD FOR PREPARING LIPID POWDER FOR USE IN PREPARING LIPOSOMES AND METHOD FOR PREPARING LIPOSOMES

[75] Inventors: Yukihiro Nanba, Kobe; Toshiya Ueno, Takasago; Toshiyuki Sakakibara, Kobe, all of Japan

[73] Assignee: 501 Nippon Fine Chemical Co., Ltd., Osaka, Japan

[21] Appl. No.: 400,147

[22] Filed: Aug. 28, 1989

[30] Foreign Application Priority Data

Aug. 29, 1988 [JP] Japan .................. 63-214542

[51] Int. Cl.$^5$ .............. B01J 13/02; A61K 9/127
[52] U.S. Cl. ..................... 264/4.1; 424/450; 159/DIG. 10
[58] Field of Search ............ 264/4.1, 4.6; 424/450; 159/2.1, 2.3, DIG. 10

[56] References Cited

U.S. PATENT DOCUMENTS

| | | | |
|---|---|---|---|
| 4,229,360 | 10/1980 | Schneider et al. | 264/4.6 |
| 4,311,712 | 1/1982 | Evans et al. | 514/773 |
| 4,508,703 | 4/1985 | Redziniak et al. | 264/4.6 X |
| 4,830,858 | 5/1989 | Payne et al. | 264/4.6 X |
| 4,935,171 | 6/1990 | Bracken | 264/4.6 |
| 4,950,432 | 8/1990 | Mehta et al. | 264/4.6 |

FOREIGN PATENT DOCUMENTS

| | | |
|---|---|---|
| 60-7932 | 1/1985 | Japan . |
| 60-7933 | 1/1985 | Japan . |
| 12127 | 1/1985 | Japan ................ 264/4.1 |
| 62-152531 | 7/1987 | Japan . |
| 62-52724 | 11/1987 | Japan . |

OTHER PUBLICATIONS

"Seiyaku Kojo", vol. 3, No. 6, pp. 299–302, 1983.
"Chemical Engineering Progress", vol. 58, No. 6, pp. 67–70, Jun. 1962.

Primary Examiner—Robert L. Stoll
Assistant Examiner—John M. Covert
Attorney, Agent, or Firm—Larson and Taylor

[57] ABSTRACT

The present invention provides
(1) a method for preparing lipid powder for use in the preparing liposome, which comprises supplying at a constant speed an organic solvent solution of lipids having liposome membrane forming ability to a tubular heater heated externally, evaporating the organic solvent in the heater to prepare a mixture substantially of solids and organic solvent vapor and introducing this mixture at a high speed into a vacuum chamber of not more than 300 mm Hg, to volatilize the organic solvent instantaneously and dry the solids, and
(2) a method for preparing liposomes comprising dispersing the lipid powder obtained by the above method (1) into an aqueous solvent.

7 Claims, 1 Drawing Sheet

METHOD FOR PREPARING LIPID POWDER FOR USE IN PREPARING LIPOSOMES AND METHOD FOR PREPARING LIPOSOMES

The present invention relates to a method for preparing lipid powder for use in preparing liposomes and a method for preparing liposomes.

BACKGROUND OF THE INVENTION

Liposomes are closed vesicles composed of lipid bilayers and can carry various substances in the inside aqueous phase or between the lipid membranes. Therefore, investigations have been undertaken to utilize as drug delivery systems liposomes with fat-soluble or amphipathic substances such as physiologically active substances (drugs etc.) entrapped therein. For example, missile therapy has been developed wherein cancer cells are selectively attacked by an anticancer agent-containing liposomes combined with a cancer surface-specific antibody.

Liposomes with a physiologically active substance entrapped therein are usually prepared by dissolving lipids which have ability to form liposome membrane, for example phospholipids, cholesterols, acidic phospholipids, etc., in an organic solvent, distilling off the solvent to some extent from this lipid solution to obtain a lipid mixture, adding an aqueous solution of the physiologically active substance to the lipid mixture and stirring the mixture vigorously. The lipid mixture according to the above method is a dense solid and can not be fully hydrated when mixed with the aqueous solution of physiologically active substance with stirring. The hydration becomes more difficult with increasing lipid concentration of the lipid mixture. Therefore, such a conventional method has various problems. More specifically, the spacing between the lipid membranes, which is very small, results in a reduced efficiency in encapsulating the physiologically active substances or reduces the encapsulating volume of the liposomes. The loss of lipids increases, i.e., the ratio of the lipids consumed for forming liposomes to the total amount of lipids used reduces. Further, defects in the lipid membrane, which frequently occur, result in reduced stability and leakage of the physiologically active substance entrapped.

In the specification, the encapsulating efficiency means the ratio of the amount of physiologically active substance entrapped to the total amount of physiologically active substance used (V/V). The encapsulating volume means the total volume of the inside aqueous phase of liposomes formed by one mole of lipids.

Furthermore, the above conventional method, when practiced industrially for mass production of liposomes aggravates the above problems, encounters difficulty in selecting the conditions for the distillation of solvent and requires a specific device for vigorous stirring to entail an increased cost. Therefore, the above conventional method has great difficulties in placing liposome compositions into practical use.

In order to overcome the above problems, various methods have been proposed.

For example, Unexamined Japanese Patent Publication No. 7933/1985 discloses a method for preferring liposomes at a higher temperature than in conventional method. By this method, however, thermolabile drugs can not be entrapped in liposomes.

Unexamined Japanese Patent Publication No. 7932/1985 discloses a method for preparing liposomes using lipids having liposome membrane forming ability in combination with polyols. However, the use of polyols leads to difficulty in homogeneously dispersing cholesterols, which are important components of the lipid membrane of liposomes, therefore gives unstable liposome membranes and permits leakage of physiologically active substances entrapped.

Unexamined Japanese Patent Publication No. 152531/1987 discloses a method for preparing liposomes comprising spray-drying into a powder a solution of lipids having liposome membrane forming ability with a spray drier and mixing the powder with an aqueous solution of physiologically active substances. However, since this powder is likely to agglutinate, it has the drawback of being difficult to hydrate. Therefore, the liposomes prepared by dissolving this powder in water is low in ability to encapsulate physiologically active substances. This method further permits an increased loss of lipids.

Furthermore, Examined Japanese Patent Publication No. 52724/1987 discloses a method for preparing liposomes carrying a pysiologically active substance, which comprises freeze-drying a solution of liposomes having liposome membrane forming ability and physioligically active substance into a powder and dissolving the powder in water. However, this method requires expensive equipment for freeze-drying, and is time-consuming to distill the solvent off, hence a greatly increased production cost.

Besides the above methods, a reverse-phase evaporation method is known, which comprises adding an aqueous solution of physiologically active substance to a solution of lipids having liposome membrane forming ability, preparing liposomes by ultrasonic emulsification and distilling the solvent. However, this method has the problem that it is difficult to distill the solvent off thoroughly and that the remaining solvent tends to give toxicity to a pharmaceutical preparation of liposomes or to inhibit the formation of liposome membrane.

SUMMARY OF THE INVENTION

An object of the present invention is to provide a method for preparing lipid powder useful for the preparation of liposomes which powder is excellent in hydration ability and can be easily hydrated on an industrially in large amounts within a short period of time.

Another object of the present invention is to provide a method for preparing lipid powder useful for the preparation of liposomes which are excellent in fat-soluble or amphipathic substance encapsulating efficiency and encapsulating volume and moreover substantially free from leakage of the fat-soluble or amphipathic substance entrapped.

A further object of the present invention is to provide a method for preparing liposomes of high quality in large quantities on an industrial scale, substantially without wasting the lipid starting material.

These objects and features of the present invention will be clarified by the following description.

DETAILED DESCRIPTION

The present invention provides (1) a method for preparing lipid powder for use in the preparing liposome, which comprises supplying at a constant speed an organic solvent solution of lipids having liposome membrane forming ability to a tubular heater heated externally, evaporating the organic solvent in the heater to prepare a mixture substantially of solids and organic solvent vapor and introducing this mixture at a high speed into a vacuum chamber of not more than 300 mm Hg, to volatilize the organic solvent instantaneously and dry the solids, and (2) a method for preparing liposomes comprising dispersing the lipid powder obtained by the above method (1) into an aqueous solvent.

The inventors found that lipid powder is excellent in hydration ability and can be easily hydrated within a short period of time even on an industrial scale, when the powder is obtained by supplying at a constant speed an organic solvent solution of lipids having liposome membrane forming ability to a tubular heater heated externally, evaporating the organic solvent in the heater to prepare a mixture substantially of solids and organic solvent vapor and introducing this mixture at a high speed into a vacuum chamber of not more than 300 mm Hg to volatilize the organic solvent instantaneously and dry the solids. The inventors further found that the liposomes prepared by hydration of said powder have high fat-soluble or amphipathic substances-encapsulating efficiency and large encapsulating volume and are substantially free from leakage of the active substances, and that the use of said powder makes it possible to prepare a large amount of liposomes of high quality on an industrial scale substantially without loss of lipids used as materials.

The present invention has been accomplished based on the above findings.

BRIEF DESCRIPTION OF THE DRAWING

The present method described above in (1) can be performed, for example, according to the flow chart as shown in FIG. 1.

First, an organic solvent of lipids having the ability to form liposome membranes is prepared, for example, by placing the lipids and organic solvent in lipid tank (1) and dissolving said lipids in an organic solvents. This operation may be done, if required, with heating.

Figure 1:
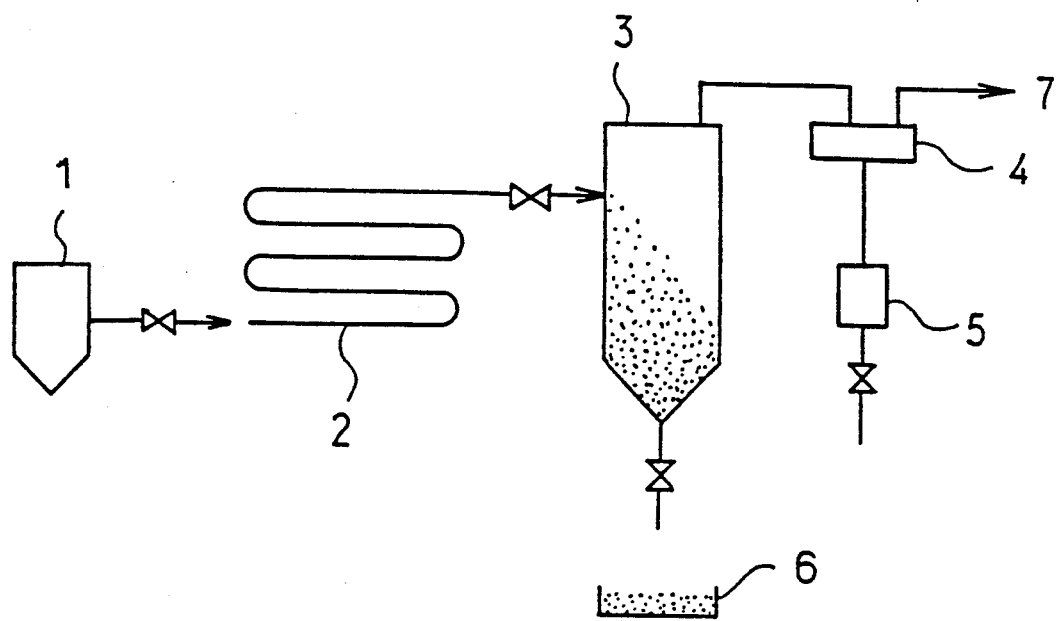

As the lipid having the liposome membrane forming ability, can be used any conventional one used for preparation of liposomes. Examples of such lipids are phospholipids, glycolipids, cholesterols, etc. Examples of phospholipids are natural phospholipids such as soybean lecithin and yolk lecithin; synthetic phospholipids such as dimyristoylphosphatidylcholine, dipalmitoylphosphatidylcholine, distearoylphosphatidylcholine, dioleylphosphatidylcholime, phosphatidyl ethanolamine, phosphatidylglycerol, sphingomyelin and phosphatidylinositol; hydrogenerated natural phospholipids such as hydrogenerated lecithin; etc. Examples of glycolipids are palmityl glycoside, stearyl glycoside, myristyl glycoside, cholesteryl maltoside, cholesteryl glycoside, ganglioside $GM_1$, $GM_2$, $GM_3$, sulfatide, etc. Examples of cholesterols are cholesterol, cholesterol acetate, dihydrocholesterol, phytosterol, sitosterol, stigmasterol, campesterol, etc.

Of the above lipids, preferable in view of the encapsulating efficiency and encapsulating volume of liposomes are dipalmitoylphosphatidylcholine, dipalmitoylphosphatidylglycerol, hydrogenerated yolk lecithin, hydrogenerated soybean lecithin, cholesterol, phytosterol, sitosterol, etc.

The above lipids may be used alone or in combination with one another. Conjoint use of two or more lipids is preferable. Such combinations are not specifically limited, and are exemplified as follows:

Dipalmitoylphosphatidylcholine: dipalmitoylphosphatidylglycerol: cholesterol = 1 : 0.001–0.5:0.01–1 (molar ratio), hydrogenerated yolk lecithin : cholesterol = 1:0.01–1, hydrogenerated soybean lecithin cholesterol = 1:0.01–1, yolk phosphatidylcholine : yolk phosphatidyl glycerol : cholesterol = 1:0.001–0.5:0.01–1, dimyristoylphosphatidylcholine : dimiristoylphophatidic acid : cholesterol = 1:0.001–0.5:0.01–1, and like combinations.

When the above lipids are used in combination with a charge-bearing substance, fusion among liposomes or leakage of the entrapped substances can be further prevented. Examples of such charge-bearing substances are charge-bearing phospholipids such as phosphatidic acid, phosphatidylserine, phosphatidylglycerol and cardiolipin; fatty acids such as myristic acid, palmitic acid and stearic acid; and potassium and sodium salts thereof.

Organic solvents are not limited specifically so far as lipids are soluble in the solvent. Typical examples are hydrocarbons such as pentane, hexane, heptane and cyclohexane; halogenated hydrocarbons such as methylene chloride and chloroform; aromatic hydrocarbons such as benzene and toluene, lower alcohols such as methanol and ethanol; esters such as methyl acetate and ethyl acetate. Such organic solvents may be used alone or in combination with one another. The amount of organic solvent is not limited and may be selected within a wide range according to the solubility of lipid in the organic solvent. In view of the use on an industrial scale, the organic solvent is used usually in an amount of about 1 to about 100 parts by weight per part by weight of the lipid to be used, and preferably about 5 to 50 parts by weight.

The lipid solution in lipid tank (1), which may be previously heated by a preheater (not shown in the drawing) if required, is supplied to tubular heater (2) at a constant rate. The method of supply is not specifically limited, so far as the solution is supplied at a constant rate, for example, using a pump or the like. The rate of supplying can be selected within a wide range, and is usually about 1 to about 100 liters/hr, preferably about 5 to about 50 liters/hr. Tubular heater (2) can be externally heated by steam heating, warm water heating , electric heating, etc. Such heating causes overheating and evaporating of the organic solvent in tubular heater (2), and then the lipid solution becomes a mixture of overheated vapor and lipids (hereinafter referred to as "solids"). At this time, a small amount of the organic solvent remains in the solids. The heating temperature is not limited specifically so far as it is higher than the boiling point of the organic solvent to be used. This temperature is usually higher than the boiling point of organic solvent by about 5° to about 100° C., and preferably by about 5° to about 50° C.

By introducing the mixture of overheated vapor and solids from the outlet of tubular heater (2) into vacuum chamber (3) of reduced pressure, the organic solvent slightly remaining in the solids is evaporated momentarily, and therefore the organic solvent does not substantially remain in the resulting solids.

The pressure in vacuum chamber (3) is generally not more than about 300 mm Hg, preferably about 5 to about 300 mm Hg and more preferably about 5 to about 100 mm Hg. The mixture of overheated vapor and solids is introduced into the vacuum chamber usually at a speed of over 0.1 times the sound speed, preferably at not less than 100 m/sec and more preferably at a speed of over the sound speed. If the pressure in the vacuum chamber is more than 300 mm Hg, tubular heater (2) will be clogged up, an increased amount of organic solvent will remain in the powder, or the large particles will be formed to reduce the hydration ability of powder, or the loss of materials will be greater. Vacuum pump (7) may be connected to vacuum chamber (3) via, for example, condenser (4) in order to evacuate chamber (3).

The above vacuum dried solids are recovered in vessel (6) placed in the lower part of vacuum chamber (3). The lipid powder for preparing liposomes of the present invention can be thus obtained. The particle size of the powder is generally about 100 to about 2000 μm. The powder obtained may be ground to a smaller particle size. The vapor obtained by volatilization of the organic solvent is liquefied in condenser (4), and the liquid is stored in recovery tank (5) to recover the organic solvent.

The present invention may employ, for example, a instantaneous vacuum drying system (trademark "CRUX", product of Orient Chemical Ind., Ltd., Japan) as a device for instantaneous vacuum drying of a lipid solution as shown in FIG. 1. Since it takes very short time, about 30 seconds to about 2 minutes, to heat materials in the above system, thermolabile lipids can be used.

Liposomes can be easily prepared by mixing the present lipid powder with an aqueous solvent. If the present lipid powder and the desired fat-soluble or amphipathic substances are mixed with an aqueous solvent, liposomes can be prepared which contain fat-soluble or amphipathic substances entrapped therein. Such aqueous solvents to be mixed with the lipid powder are not specifically limited, and include aqueous solutions of inorganic salts such as sodium chloride and potassium chloride, aqueous solutions of sugars such as glucose, maltose, sucrose and trehalose, distilled water, etc. Fat-soluble or amphipathic substances are not specifically limited. The amount of the lipid powder is not specifically limited, but is generally about 0.1 to about 30 wt. %, preferably about 0.1 to about 10 wt. %, based on the total amount of the powder and the aqueous solvent. Mixing may be done with a conventional agitator Conventional osmoregulators such as glucose and sodium chloride may be added if required, on mixing.

The present inventors also found that, when liposomes are prepared using the lipid powder produced by dissolving fat-soluble or amphipathic substances in an organic solvent solution of lipids having liposome membrane forming ability and vacuum drying in the same manner as above, substantially all the fat-soluble or amphipathic substances used are efficiently entrapped in the liposomes.

The fat-soluble or amphipathic substances include physiologically active substances such as drugs, proteins, enzymes, hormones, vitamines and extracts of animals or plants, labeling substances such as fluorescent substances, radioactive substances, labeled compounds and colors etc. The amount of the physiologically active substances to be added to the above organic solvent its not specifically limited.

The present invention will be described in more detail with reference to the following examples and comparative examples.

EXAMPLE 1

A 600 g quantity of completely hydrogenerated purified yolk lecithin, 300 g of cholesterol and 90 g of completely hydrogenerated yolk phosphatidylglycerol were dissolved in 10 liters of chloroform. This solution was evaporated to dryness using an instantaneous vacuum drying system (trademark "CRUX 8B", product of Orient Chemical Ind., Ltd., Japan, hereinafter referred to as "CRUX system").

More specifically, the above solution was placed into liquid tank (1), from which the solution was fed to the tubular heater (2) at a flow rate of 12 liters/h, which setting the heat exchanger placed around tubular heater (2) at a temperature of 70° C. and vacuum chamber (3) at a vacuum of 60 to 70 mm Hg for drying. The mixture of chloroform vapor and lipids flowed out from tubular heater (2) into vacuum chamber (3) at a speed of over 0.1 times the sound speed. Operation for 40 minutes, afforded 50 g of white fine powder (recovery rate of lipids: 95%).

When a portion of the powder obtained was dried for 6 hours at room temperature in vacuo at up to 0.1 mm Hg, the resulting weight loss was not more than 0.1%. The organic solvent was almost completely distilled off by instantaneous vacuum drying using CRUX system.

In order to evaluate the liposome membrane forming ability of the white fine powder, liposomes were prepared by the following method.

One gram of the powder was placed into an appropriate glass vessel, and 95 ml of an aqueous solution of 0.15 M sodium chloride and 2 ml of an aqueous solution of 200 mM carboxyfluorescein (referred to as "CF") were added thereto in order to give an adjusted lipid concentration of 165 mM. The mixture was stirred at 10000 rpm at 45° C. for 20 minutes with a homogenizer, giving a homogeneous liposome suspension.

The suspension was separated using Sephadex G-50 Column (product of Pharmacia Fine Chemicals) into liposomes and CF which was not entrapped in the liposomes. The encapsulating efficiency and encapsulating volume of the liposomes were 55% and 3.5 liters/mole, respectively.

In order to test the stability of the isolated liposomes/ a quantity of the liposomes were incubated at 37° C. in an aqueous solution of 0.15M NaCl. Subsequently, by determining the fluorescence intensity of the supernatant obtained, leakage of the CF entrapped was monitered with time.

The rate of leakage (%) was calculated from the following equation:

$$\text{Rate of leakage} = \frac{A - B}{8.0 - B}$$

A: Fluorescence intensity determined
B: Fluorescence intensity at 0 hour

In the above equation, "8.0" was fluorescence intensity determined when liposomes were completely destroyed by adding 10% Triton X-100 (product of Pierce Co.) to the specimen incubated. The result is shown in Table 1 below.

COMPARATIVE EXAMPLE 1

The same components as in Example 1 were used except that their amounts were 1/100 times the amounts used in Example 1. The components were dissolved in 100 ml of chloroform, and the solvent was distilled off using a rotary evaporator. The resulting product was allowed to stand under reduced pressure of 1 mm Hg for three hours to evaporate chloroform thoroughly. The recovery rate of lipids was 100%.

When the residue was treated in the same manner as in Example 1, the weight loss was 3%. The residue was placed into a glass vessel, and 95 ml of an aqueous solution of 0.15 M NaCl and 5 ml of an aqueous solution of mM CF were added thereto, followed by stirring at rpm at 45° C. for 20 minutes with a homogenizer. Solid substances still remained at this time, so the mixture was further stirred for 15 minutes to give a homogeneous suspension of liposomes.

The encapsulating efficiency and encapsulating volume of the liposomes obtained were 18% and 1.3 liters/mole, respectively. The leakage rate (%) of liposomes was calculated according to Example 1. The result is shown in Table 1.

TABLE 1

| Time (hour) | Example 1 | | Comparative Example 1 | |
|---|---|---|---|---|
| | Fluorescence intensity | Leakage rate | Fluorescence intensity | Leakage rate |
| 0 | 0.01 | 0 | 0.01 | 0 |
| 1 | 0.024 | 0.3 | 0.048 | 0.6 |
| 2 | 0.040 | 0.5 | 0.080 | 1 |
| 6 | 0.056 | 0.7 | 0.184 | 2.3 |
| 24 | 0.056 | 0.7 | 0.368 | 4.6 |
| 48 | 0.056 | 0.7 | 0.464 | 5.8 |

Table 1 reveales that the present liposomes are much more excellent than those obtained by the conventional method in encapsulating efficiency, encapsulating volume and stability. Since satisfactory results were obtained in Example 1 in spite of large amounts of the materials, the present method proved to be applicable to mass production of liposomes.

COMPARATIVE EXAMPLE 2

The same components as in Example 1 were used except that their amounts were 1/100 times as large as those in Example 1. The components were dissolved in 100 ml of chloroform, and the solution was dried using a spray drier (EYELA SD-1, product of Tokyo Rika Kikai Ltd., Japan) under the conditions of an air pressure of 1.0 kg/cm$^2$, a flow rate of about 9 g/min, a chamber inlet temperature of 65° C. and a chamber outlet temperature of 50° C. A 5.9 g quantity of white powder was obtained with a recovery rate of lipids of 60%. The weight loss on drying of this powder was 1.3%.

In order to evaluate the liposome forming ability of the powder, 95 ml of aqueous NaCl (0.15M) and 2 ml of aqueous CF (200 mM) were added to 1 g of the powder to give an adjusted lipid concentration of 165 mM. The liposome suspension was prepared in the same manner as in Example 1. The encapsulating efficiency and encapsulating volume were 20% and 0.6 liter/mole, respectively. The leakage rate was 3% after 48 hours.

EXAMPLE 2

A 600 g quantity of dimyristoylphosphatidylcholine, 200 g of cholesterol and 60 g of dimyristoylphophatidyl glycerol were dissolved in 9 liters of benzene. The following operation was conducted in the same manner as in Example 1 except that the temperature of heat exchanger was 80° C. (the mixture of benzene vapor and lipids flowed at a speed of over 0.1 times the sound speed from the tubular heater to the vacuum chamber), affording 810.1 g of white powder (recovery rate of lipids: 94.2%, weight loss on drying: not more than 0.1%).

In order to evaluate the liposome forming ability of the powder, the powder was treated in the same manner as in Example 1 to give a liposome suspension. The encapsulating efficiency and encapsulating volume of the liposomes were 33% and 2.1 liters/mole, respectively. The leakage rate (%) was calculated according to Example 1, and the result is shown in Table 2.

COMPARATIVE EXAMPLE 3

The same components as in Example 2 were dissolved in 80 ml of benzene with the proviso that their amounts were 1/100 times the amounts used in Example 1. The solution was dried using a spray drier (EYELA SD-1, product of Tokyo Rika Kikai Ltd., Japan) under the conditions of an air pressure of 1.0 kg/cm$^2$, a flow rate of about 8 g/min, a chamber inlet temperature of 75° C. and a chamber outlet temperature of 60° C. A 5.1 g quantity of white powder was obtained with a recovery rate of lipids of 65%. This powder partly agglutinated into large particles. The weight loss on drying of this powder was 1.5%.

In order to evaluate the liposome forming ability of the powder, 95 ml of aqueous NaCl (0.15 M) and 5 ml of aqueous CF (200 mM) were added to 1 g of the powder. The mixture was stirred at 10000 rpm at 45° C. for 17 minutes using a homogenizer to give a liposome suspension. The encapsulating efficiency and encapsulating volume of the liposomes obtained were 22% and 1.5 liters/mole, respectively. The stability of this liposome was evaluated in the same manner as in Example 1, and the result is shown in Table 2.

TABLE 2

| Time (hour) | Example 2 | | Comparative Example 2 | |
|---|---|---|---|---|
| | Fluorescence intensity | Leakage rate | Fluorescence intensity | Leakage rate |
| 0 | — | 0 | — | 0.01 |
| 1 | 0.032 | 0.4 | 0.056 | 0.7 |
| 2 | 0.048 | 0.6 | 0.096 | 1.2 |
| 6 | 0.064 | 0.8 | 0.160 | 2.0 |
| 24 | 0.056 | 0.7 | 0.320 | 4.0 |
| 48 | 0.064 | 0.8 | 0.488 | 6.1 |

Table 2 reveals that the present liposomes are much more excellent than those obtained by the conventional method in encapsulating efficiency, encapsulating volume and stability.

EXAMPLE 3

The lipid powder was prepared in the same manner as in Example 2 except that 522 g (750 mM) of dimyristoylphosphatidylcholine, 2.9 g (750 mM) of cholesterol and 53 g (75 mM) of dimyristoylphophatidyl glycerol were used (the mixture of benzene vapor and lipids flowed at a speed of over 0.1 times the sound speed from the tubular heater into the vacuum chamber), affording white powder.

In order to evaluate the liposome forming ability of the powder, 9 ml of aqueous glucose (0.3M) and 1.1 ml of aqueous CF (200 mM) were added to 3 g of the powder to give an adjusted lipid concentration of 495 mM. The liposome solution was prepared in the same manner as in Example 2. The encapsulating efficiency and encapsulating volume of the liposomes obtained were 55% and 1.1 liters/mole, respectively.

COMPARATIVE EXAMPLE 4

To 3 g of the powder used for preparation of liposomes, 19 ml of aqueous glucose (0.3 M) and 1 ml of aqueous CF (200 mM) were added to give an adjust lipid concentration of 495 mM. The liposome suspension was prepared in the same manner as in Example 1. The encapsulating efficiency and encapsulating volume of the liposomes obtained were 36% and 0.78 liter/mole, respectively.

EXAMPLE 4

A 600 g quantity of completely hydrogenerated soybean lecithin, 300 g of cholesterol and 300 g of vitamin E acetate (tocopherol acetate) were dissolved in liters of chloroform. The solution was subjected to vacuum drying in the same manner as in Example 1, affoding powder.

One gram of this powder was placed in a glass vessel, and thereto was added 9 ml of an aqueous solution of 0.15M NaCl. The mixture was stirred at 10000 rpm at 45° C. for 20 minutes using a homogenizer, giving a homogeneous liposome suspension.

The suspension was separated into a layer of liposomes and a layer of substances other than liposomes. The latter layer did not contain vitamin E acetate. All the vitamin E acetate seemed to be entrapped in the liposomes.

What is claimed is:

1. A method for preparing liposomes comprising the steps of:
   i) supplying at a constant speed an organic solvent solution of a mixture of lipids having liposome membrane forming ability to a tubular heater heated externally,
   ii) evaporating the organic solvent in the heater to prepare a mixture substantially of solids and overheated organic solvent vapor,
   iii) introducing this mixture at a high speed of over 0.1 times the sound speed into the vacuum chamber of not more than 300 mm Hg to volatilize the organic solvent instantaneously and dry the solids, whereby lipid powder is obtained, and
   iv) dispersing the resulting lipid powder into an aqueous solvent.

2. A method according to claim 1 comprising dispersing into an aqueous solvent the resultant lipid power and a desired fat-soluble or amphipathic substance simultaneously.

3. A method according to claim 1 in which the aqueous solvent is one member selected from the group consisting of water, an aqueous solution of inorganic salts, and an aqueous solution of sugar or water.

4. A method according to claim 1 in which said lipid mixture is a mixture of lipids selected from the group consisting of phospholipids, glycolipids and cholesterols.

5. A method according to claim 4 in which said phospholipid is one member selected from the group consisting of lecithin, yolk lecithin, dimyristoylphospharidylcholine, dipalmitoylphosphatidylcholine, distearoylphosphatidylcholine, dioleylphosphatidylcholine, phosphatidyl ethanolamine, phosphatidylglycerol, sphingomyelin and phosphatidylinositol and hydrogenated lecithin; said glycolipid is one member selected from the group consisting of myristyl glycoside, cholesteryl glycoside, ganglioside $GM_1$, ganglioside $GM_3$ and sulfatide; and said cholesterol is one member selected from the group consisting of cholesterol, cholesterol acetate, dihydrocholesterol, phytosterol, sitosterol, stigmasterol and campesterol.

6. A method according to claim 4 in which said lipid mixture is a mixture of cholesterol and lipids other than cholesterols.

7. A method according to claim 6 in which said lipid mixture comprises a mixture of:
   a) dipalmitoylphosphatidylcholine, dipalmitoylphosphatidylglycerol and cholesterol,
   b) hydrogenated yolk lecithin and cholesterol,
   c) hydrogenated soybean lecithin and cholesterol,
   d) yolk phosphatidylcholine, yolk phosphatidyl glycerol and cholesterol,
   e) dimyristoylphosphatidylcholine, dimiristoylphosphatidic acid and cholesterol,
   f) hydrogenated yolk lecithin, hydrogenated yolk phospatidylglycerol and cholesterol, or
   g) dimyristoylphoshatidylcholine, dimyristoylphosphatidylglycerol and cholesterol.

* * * * *